(12) United States Patent
Sasaki

(10) Patent No.: US 8,001,984 B2
(45) Date of Patent: Aug. 23, 2011

(54) LAPAROSCOPIC LENS CLEANER

(76) Inventor: Larry S. Sasaki, Shreveport, LA (US)

( * ) Notice: Subject to any disclaimer, the term of this patent is extended or adjusted under 35 U.S.C. 154(b) by 620 days.

(21) Appl. No.: 11/810,081

(22) Filed: Jun. 4, 2007

(65) Prior Publication Data

US 2007/0282253 A1    Dec. 6, 2007

Related U.S. Application Data

(60) Provisional application No. 60/811,073, filed on Jun. 6, 2006.

(51) Int. Cl.
  *B08B 3/00* (2006.01)
  *A61B 1/12* (2006.01)
(52) U.S. Cl. ............ 134/95.2; 134/94.1; 134/95.1; 134/95.3; 134/99.1; 134/102.1; 600/157; 600/158; 600/159
(58) Field of Classification Search ............ 600/157, 600/158, 159; 134/95.2, 94.1, 95.1, 95.3, 134/99.1, 102.1
See application file for complete search history.

(56) References Cited

U.S. PATENT DOCUMENTS

| | | | |
|---|---|---|---|
| 4,281,646 A | 8/1981 | Kinoshita | 128/6 |
| 4,497,550 A * | 2/1985 | Ouchi et al. | 359/509 |
| 4,748,970 A * | 6/1988 | Nakajima | 600/158 |
| 5,215,531 A * | 6/1993 | Maxson et al. | 604/180 |
| 5,228,625 A * | 7/1993 | Grassberger | 239/558 |
| 5,386,817 A * | 2/1995 | Jones | 600/104 |
| 5,392,766 A | 2/1995 | Masterson et al. | 128/4 |
| 5,400,767 A * | 3/1995 | Murdoch | 600/157 |
| 5,464,008 A * | 11/1995 | Kim | 600/157 |
| 5,563,737 A | 10/1996 | Kamrat | 359/509 |
| 5,575,756 A * | 11/1996 | Karasawa et al. | 600/157 |
| 5,630,795 A * | 5/1997 | Kuramoto et al. | 604/30 |
| 6,409,657 B1 | 6/2002 | Kawand | 600/157 |
| 6,638,214 B2 | 10/2003 | Akiba | 600/157 |
| 6,712,757 B2 * | 3/2004 | Becker et al. | 600/121 |
| 2004/0220452 A1 | 11/2004 | Shalman | 600/157 |

* cited by examiner

*Primary Examiner* — Michael Barr
*Assistant Examiner* — Charles W Kling
(74) *Attorney, Agent, or Firm* — R. Keith Harrison; John M. Harrison

(57) ABSTRACT

A laparoscopic lens cleaner which is suitable for maintaining the lens of a laparoscope in a clean, dry condition during a laparoscopic surgical procedure is disclosed. An illustrative embodiment of the laparoscopic lens cleaner includes an elongated cleaner sheath having a sheath interior, a fluid conduit provided in the cleaner sheath, a fluid discharge nozzle provided in the sheath interior and communicating with the fluid conduit, a gas conduit provided in the cleaner sheath and a gas discharge nozzle provided in the sheath interior and communicating with the gas conduit.

17 Claims, 4 Drawing Sheets

LAPAROSCOPIC LENS CLEANER

CROSS-REFERENCE TO RELATED APPLICATIONS

This application claims the benefit of and incorporates by reference in its entirety prior filed copending U.S. Provisional application Ser. No. 60/811,073, filed Jun. 6, 2006.

FIELD

The present disclosure relates to laparoscopes. More particularly, the present disclosure relates to a laparoscopic lens cleaner which is fitted over a laparoscope to maintain the lens of the laparoscope in a clean, dry condition during a laparoscopic surgical procedure.

BACKGROUND

Laparoscopes are surgical instruments through which anatomical structures in the abdomen and pelvis can be viewed by a surgeon. Laparoscopic surgery has become increasingly popular in recent years because it eliminates the need to cut a large surgical incision in a patient. This reduces patient recovery time and discomfort as well as the deleterious side effects associated with major surgery. In a laparoscopic surgical procedure, a small incision is initially cut in the abdominal wall of the patient to facilitate insertion of the laparoscope into the patient's abdomen or pelvis. Cannula sleeves can be inserted into the same incision or an adjacent incision or incisions to serve as entry ports for the extension of probes and other laparoscopic surgical instruments into the abdomen or pelvis. Laparoscopic surgery can be used to repair or remove internal tissues or organs as well as to aid in diagnostics since the contents of the abdomen or pelvis, including such anatomical structures as the fallopian tubes, ovaries, uterus, small and large intestines, appendix, liver and gallbladder, for example, can be viewed through the laparoscope.

A typical laparoscope includes a housing. An elongated lens shaft extends from one end of the housing, and a lens is provided in the distal end of the lens shaft. A camera viewfinder extends from the other end of the housing. A camera is connected to the housing and transmits images sighted through the lens to a television monitor on which the images are displayed. During a surgical procedure, the distal end portion of the lens shaft is extended into an incision in the patient's abdominal wall, while the proximal end portion of the lens shaft, the housing and the camera viewfinder remain outside the patient. One of the limitations of conventional laparoscopes is that the laparoscope lens frequently contacts and is obscured by blood, tissue and other matter during a laparoscopic surgical procedure. This adversely affects the quality of the images displayed on the television monitor.

SUMMARY

The present disclosure is generally directed to a laparoscopic lens cleaner which is suitable for maintaining the lens of a laparoscope in a clean, dry condition during a laparoscopic surgical procedure. An illustrative embodiment of the laparoscopic lens cleaner includes an elongated cleaner sheath having a sheath interior, a fluid conduit provided in the cleaner sheath, a fluid discharge nozzle provided in the sheath interior and communicating with the fluid conduit, a gas conduit provided in the cleaner sheath and a gas discharge nozzle provided in the sheath interior and communicating with the gas conduit.

BRIEF DESCRIPTION OF THE DRAWINGS

The disclosure will now be made, by way of example, with reference to the accompanying drawings, in which.

DETAILED DESCRIPTION

Figure 1:
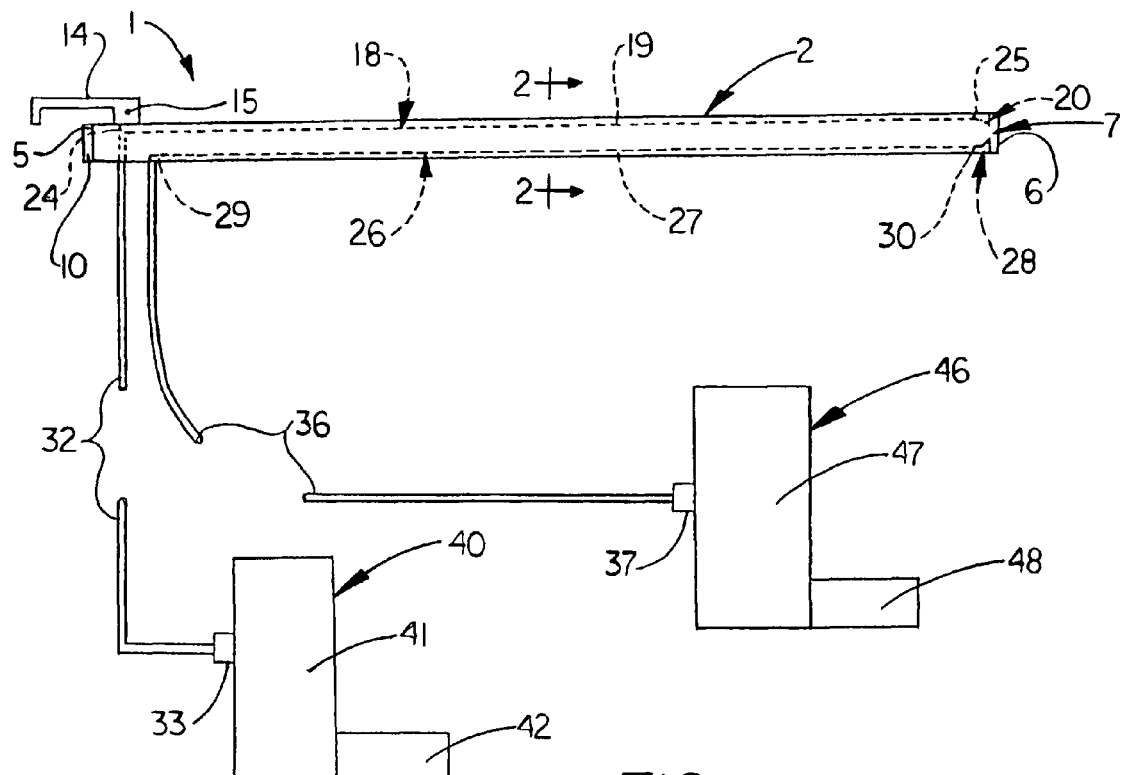
FIG. 1 is a side, partially schematic view of an illustrative embodiment of the laparoscopic lens cleaner according to the present disclosure, with a fluid pump and supply apparatus and a gas pump and supply apparatus connected to the laparoscopic lens cleaner through respective connecting conduits (partially in section)
Figure 2:
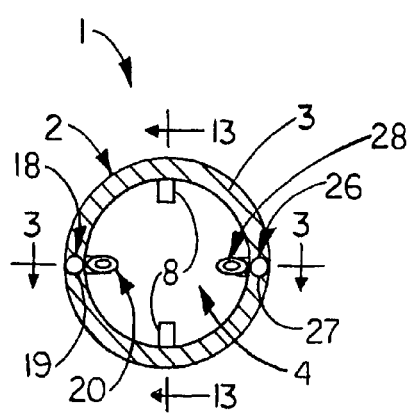
FIG. 2 is a cross-sectional view, taken along section lines 2-2 in FIG. 1, of a cleaner sheath element of the laparoscopic lens cleaner.
Figure 3:
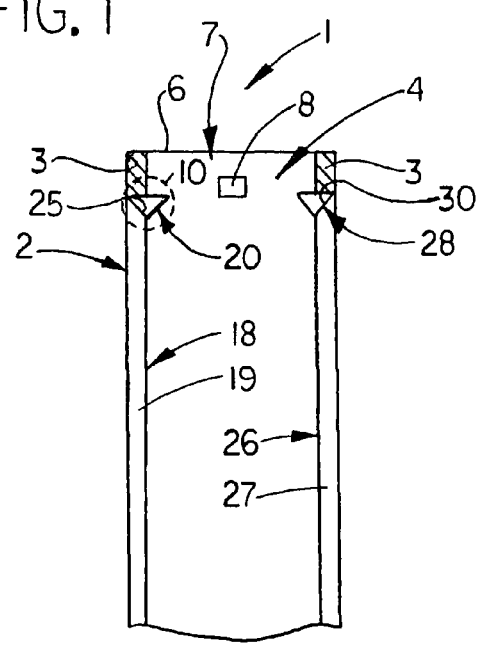
FIG. 3 is a longitudinal sectional view, partially in section, taken along section lines 3-3 in FIG. 2, of the cleaner sheath element of the laparoscopic lens cleaner.

Referring initially to FIGS. 1-4 and 10-13 of the drawings, an illustrative embodiment of the laparoscopic lens cleaner according to the present disclosure is generally indicated by reference numeral 1. The laparoscopic lens cleaner 1 includes a generally elongated, cylindrical or tubular cleaner sheath 2 having a sheath wall 3 which may be a substantially rigid or semi-rigid plastic, for example. As illustrated in FIG. 2, the sheath wall 3 typically has a generally annular cross-sectional configuration and defines a sheath interior 4. As illustrated in FIG. 1, the cleaner sheath 2 has a proximal end 5 and a distal end 6 having a distal opening 7. As illustrated in FIGS. 2 and 3, at least one sheath flange 8, the purpose of which will be hereinafter described, may extend from the sheath wall 3 and into the sheath interior 4, generally at or adjacent to the distal end 6 of the cleaner sheath 2. As illustrated in FIG. 2, a pair of sheath flanges 8 may extend from the sheath wall 3 and into the sheath interior 4, typically in generally diametrically-opposed relationship to each other.

As illustrated in FIG. 1, an attachment clip 14 of selected design may be provided on the cleaner sheath 2, adjacent to the proximal end 5 of the cleaner sheath 2, to facilitate detachable attachment of the laparoscopic lens cleaner 1 to a laparoscope 56 (FIGS. 5 and 6) in typical use of the laparoscopic lens cleaner 1, as will be hereinafter described. The attachment clip 14 may be pivotally attached to the cleaner sheath 2 by a pivot pin 15. The typically spring-loaded attachment clip 14 is normally biased in the locking configuration which is indicated by the solid lines in FIG. 5 and may be pivoted against the spring-loaded bias to an unlocking configuration which is indicated by the phantom lines in FIG. 5. As illustrated in FIG. 1, a ring gasket 10 may be provided on the proximal end 5 of the cleaner sheath 2 to provide a seal between the cleaner sheath 2 and the laparoscope 56 when the laparoscopic lens cleaner 1 is provided on the laparoscope 56, as will be hereinafter described.

A fluid conduit 18 is provided in the cleaner sheath 2 and includes an elongated fluid distribution segment 19 which extends generally parallel to the longitudinal axis of the cleaner sheath 2. As illustrated in FIG. 1, the fluid distribution segment 19 has an inlet end 24 which is typically at or adjacent to the proximal end 5 of the cleaner sheath 2 and an outlet end 25 which terminates adjacent to the distal end 6 of the cleaner sheath 2. As illustrated in FIG. 2, the fluid distribution segment 19 of the fluid conduit 18 typically extends within and along the sheath wall 3 of the cleaner sheath 2. The diameter or width of the fluid distribution segment 19 may be substantially equal to or slightly larger than the thickness of the sheath wall 3.

Figure 10:
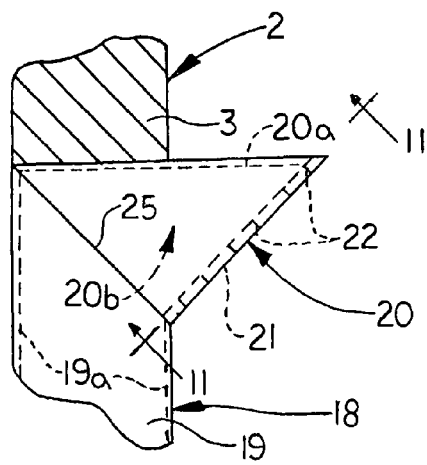
FIG. 10 is an enlarged sectional view, taken along section line 10 in FIG. 3, of a fluid discharge nozzle element of the laparoscopic lens cleaner.
Figure 11:
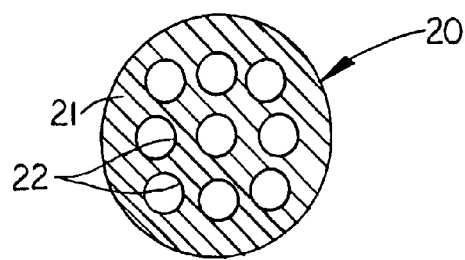
FIG. 11 is a cross-sectional view, taken along section lines 11-11 in FIG. 10, of a fluid discharge nozzle element of the laparoscopic lens cleaner, more particularly illustrating a multi-nozzle opening embodiment of the laparoscopic lens cleaner.
Figure 12:
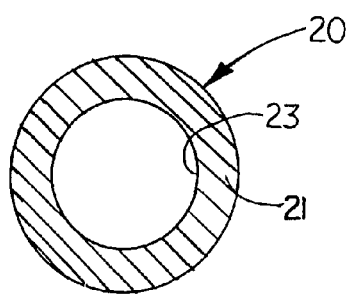
FIG. 12 is a cross-sectional view, taken along section lines 11-11 in FIG. 10, of a fluid discharge nozzle element of the laparoscopic lens cleaner, more particularly illustrating a single-nozzle opening embodiment of the laparoscopic lens cleaner.

As illustrated in FIG. 3, a fluid discharge nozzle 20 communicates with the outlet end 25 of the fluid distribution segment 19 and protrudes into the sheath interior 4, typically adjacent to the distal end 6 of the cleaner sheath 2. As illustrated in FIG. 10, the fluid discharge nozzle 20 has a nozzle wall 20a which is continuous with a segment wall 19a of the fluid distribution segment 19 and defines a nozzle interior 20b. The nozzle interior 20b of the fluid discharge nozzle 20 communicates with the fluid distribution segment 19. A nozzle plate 21 is provided in the nozzle interior 20b. As illustrated in FIG. 11, in some embodiments of the laparoscopic lens cleaner 1, multiple nozzle openings 22 extend through the nozzle plate 21 in a selected pattern to form a spray configuration of a cleaning fluid 50 (FIG. 4) as the cleaning fluid 50 is ejected through the nozzle openings 22, in use of the laparoscopic lens cleaner 1 as will be hereinafter described. As illustrated in FIG. 12, in other embodiments of the laparoscopic lens cleaner 1, a single nozzle opening 23 extends typically through the central portion of the nozzle plate 21 to form a single stream configuration of the cleaning fluid 50 as the cleaning fluid 50 is ejected through the nozzle opening 23. As illustrated in FIG. 1, a typically elongated, flexible fluid connecting conduit 32, which may be fitted with a conduit connector 33, is disposed in fluid communication with the inlet end 24 of the fluid distribution segment 19 and extends from the cleaner sheath 2 for purposes which will be hereinafter described.

A gas conduit 26 is further provided in the cleaner sheath 2 and includes an elongated gas distribution segment 27 which extends generally parallel to the longitudinal axis of the cleaner sheath 2. As illustrated in FIG. 1, the gas distribution segment 27 has an inlet end 29 which is typically at or adjacent to the proximal end 5 and an outlet end 30 which terminates typically adjacent to the distal end 6 of the cleaner sheath 2. As illustrated in FIG. 2, like the fluid distribution segment 19 of the fluid conduit 18, the gas distribution segment 27 of the gas conduit 26 typically extends within and along the sheath wall 3 of the cleaner sheath 2. The diameter or width of the gas distribution segment 27 may be substantially equal to or slightly larger than the thickness of the sheath wall 3. As further illustrated in FIG. 2, the gas distribution segment 27 of the gas conduit 26 may be positioned in generally diametrically-opposed relationship to the fluid distribution segment 19 of the fluid conduit 18, on the opposite side of the sheath interior 4. As illustrated in FIGS. 2 and 3, a gas discharge nozzle 28, which may have the same design as the fluid discharge nozzle 20, communicates with the outlet end 30 of the gas distribution segment 27 and protrudes into the sheath interior 4. As illustrated in FIG. 1, a typically elongated, flexible gas connecting conduit 36, which may be fitted with a conduit connector 37, is disposed in fluid communication with the inlet end 29 of the gas distribution segment 27 and extends from the cleaner sheath 2 for purposes which will be hereinafter described.

Figure 4:
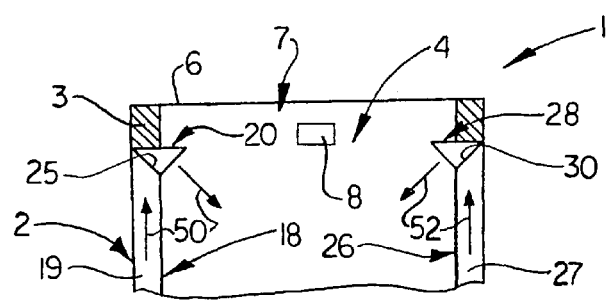
FIG. 4 is a longitudinal sectional view, partially in section, taken along section lines 3-3 in FIG. 2, of the cleaner sheath element of the laparoscopic lens cleaner, more particularly illustrating typical discharging of a cleaning fluid and a drying gas from respective discharge nozzles provided in the cleaner sheath element in typical use of the laparoscopic lens cleaner.

As further illustrated in FIG. 1, the fluid connecting conduit 32 is adapted for connection to a discharge outlet (not illustrated) of a fluid pump and supply apparatus 40, according to the knowledge of those skilled in the art, such as through the conduit connector 33 provided on the fluid connecting conduit 32, for example. The fluid pump and supply apparatus 40 may be conventional and includes a fluid reservoir 41 which is adapted to contain a cleaning fluid 50 (FIG. 4) such as saline solution, for example. The fluid pump and supply apparatus 40 typically further includes a foot pedal 42 which can be depressed to discharge the cleaning fluid 50 under pressure from the fluid reservoir 41 and into the fluid connecting conduit 32. Accordingly, responsive to depression of the foot pedal 42, the cleaning fluid 50 is discharged under pressure from the fluid pump and supply apparatus 40 and flows through the fluid connecting conduit 32 and the fluid distribution segment 19 of the fluid conduit 18, respectively. The cleaning fluid 50 is then discharged from the fluid discharge nozzle 20 into the sheath interior 4 of the cleaning sheath 2, as illustrated in FIG. 4, for purposes which will be hereinafter described.

The gas connecting conduit 36 is adapted for connection to an outlet of a gas pump and supply apparatus 46, according to the knowledge of those skilled in the art, such as through the conduit connector 37 provided on the gas connecting conduit 36, for example. The gas pump and supply apparatus 46, like the fluid pump and supply apparatus 40, may be conventional and includes a gas reservoir 47 which is adapted to contain a drying gas 52 (FIG. 4) such as carbon dioxide, for example. The gas pump and supply apparatus 46 typically further includes a foot pedal 48 which can be depressed to discharge the drying gas 52 under pressure from the gas reservoir 47 and into the gas connecting conduit 36. Accordingly, responsive to depression of the foot pedal 48, the drying gas 52 is discharged under pressure from the gas pump and supply apparatus 46 and flows through the gas connecting conduit 36 and the gas distribution segment 27 of the gas conduit 26, respectively. The drying gas 52 is then discharged from the gas discharge nozzle 28 into the sheath interior 4 of the cleaning sheath 2, as illustrated in FIG. 4, for purposes which will be hereinafter described. It is to be understood that the fluid pump and supply apparatus 40 and/or the gas pump and supply apparatus 46, instead of being foot-operated, may alternatively be any type of trigger-operated, button-operated or programmable apparatus known by those skilled in the art which is capable of containing and dispensing a cleaning fluid 50 and/or a drying gas 52, respectively, under pressure in a manually-controlled or automatic fashion.

Figure 5:
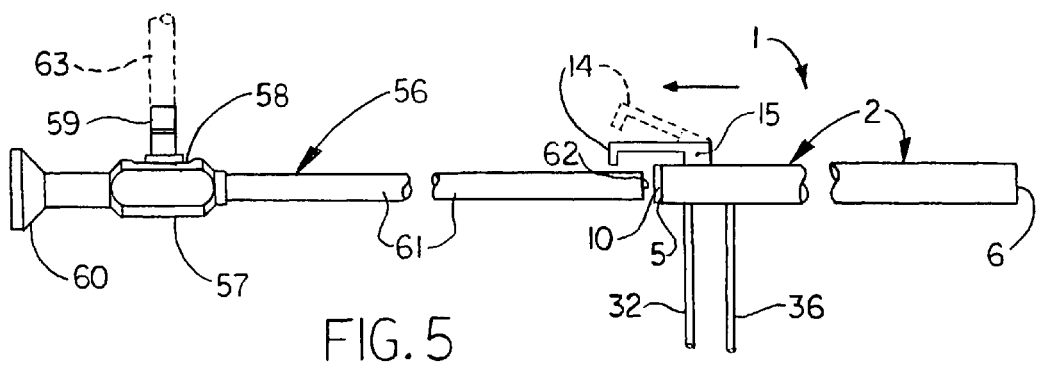
FIG. 5 is a side view, partially in section, of a laparoscope, preparatory to placement of an illustrative embodiment of the laparoscopic lens cleaner, partially in section, on the laparoscope in typical application of the laparoscopic lens cleaner.
Figure 6:
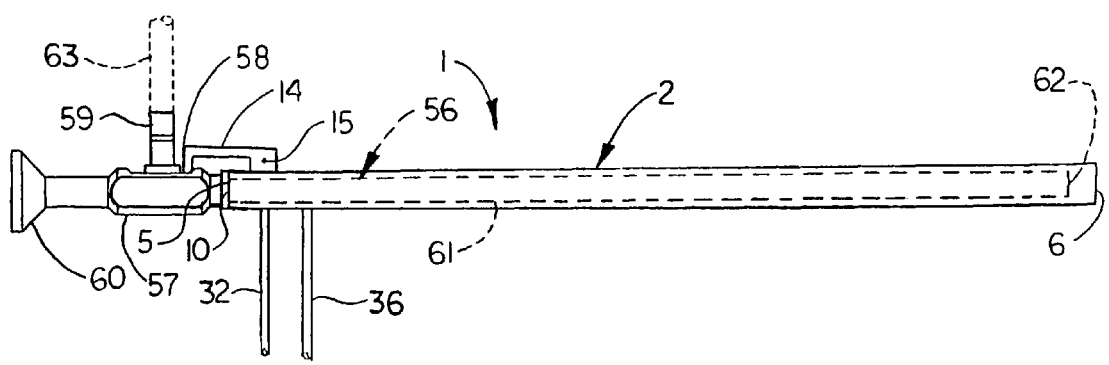
FIG. 6 is a side view, partially in section, of a laparoscope, with an illustrative embodiment of the laparoscopic lens cleaner fitted on the laparoscope in typical application of the laparoscopic lens cleaner.

Referring again to FIG. 1 and to FIGS. 5-9 and 13 of the drawings, in typical use, the laparoscopic lens cleaner 1 is provided on a laparoscope 56 (FIGS. 5 and 6) to periodically clean and dry a laparoscope lens 62 of the laparoscope 56 during a laparoscopic surgical procedure. As illustrated in FIGS. 5 and 6, the laparoscope 56 may be conventional and typically includes a laparoscope housing 57. A camera viewfinder 60 extends typically from one end of the laparoscope housing 57. An elongated lens shaft 61 extends typically from the end of the laparoscope housing 57 which is opposite the camera viewfinder 60. The laparoscope lens 62 is provided in the extending or distal end of the lens shaft 61. A camera attachment nipple 59 may extend from the laparoscope housing 57, typically between the camera viewfinder 60 and the lens shaft 61. The camera attachment nipple 59 is adapted for connection to a camera cord 63 which is, in turn, connected to a laparoscope camera (not illustrated). In typical use of the laparoscope 56, the viewfinder 60 is adapted to sight images of a surgical field typically in the abdominal or pelvic region of a patient 66 (FIG. 7) as the position of the laparoscope 56 is initially adjusted to view a particular anatomical structure or structures in the surgical field. The laparoscope camera, typically connected to the camera attachment nipple 59 through the camera cord 63, is adapted to receive images of the surgical field sighted through the laparoscope lens 62 and transmit the images to a television monitor (not illustrated) which is connected to the laparoscope camera and on which the images of the surgical field are displayed. Accordingly, the television monitor enables a surgical team to view the anatomical structure or structures in the surgical field inside the patient as the surgical procedure is carried out using laparoscopic surgical instruments.

Figure 8:
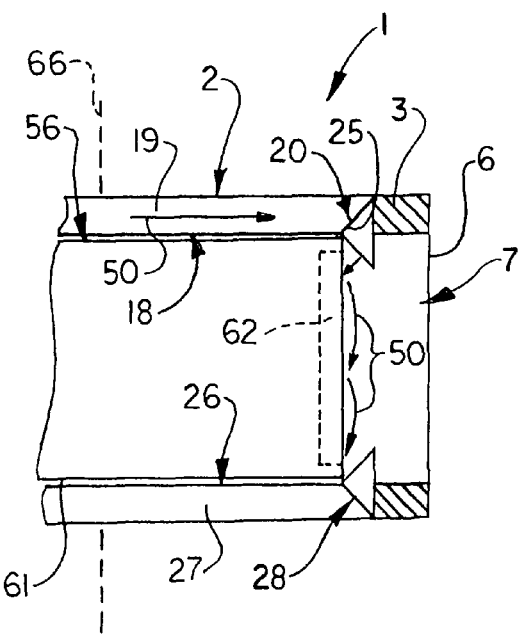
FIG. 8 is an enlarged longitudinal sectional view, partially in section, taken along section lines 3-3 in FIG. 2, of the cleaner sheath element of the laparoscopic lens cleaner, with the laparoscopic lens cleaner fitted on a laparoscope and more particularly illustrating typical discharging of a cleaning fluid from the laparoscopic lens cleaner and against the lens of the laparoscope.
Figure 9:
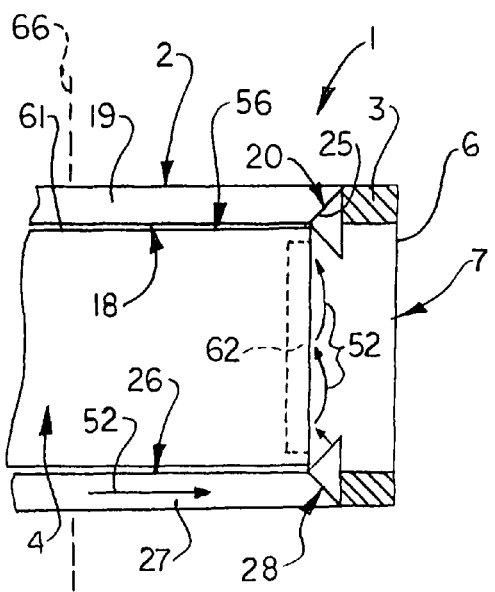
FIG. 9 is an enlarged longitudinal sectional view, partially in section, taken along section lines 3-3 in FIG. 2, of the cleaner sheath element of the laparoscopic lens cleaner, with the laparoscopic lens cleaner fitted on a laparoscope and more particularly illustrating typical discharging of a drying gas from the laparoscopic lens cleaner and against the lens of the laparoscope.
Figure 13:
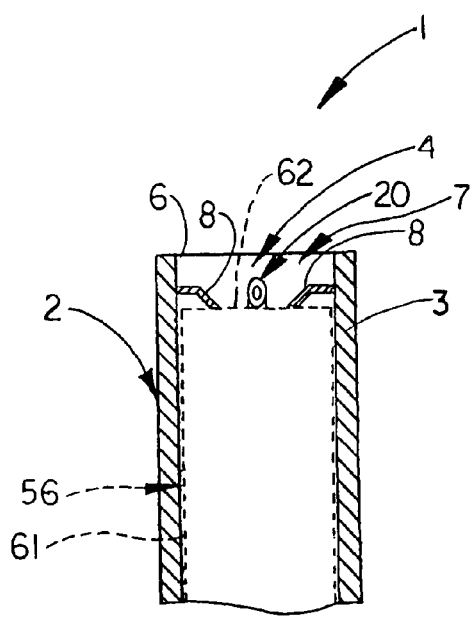
FIG. 13 is a longitudinal sectional view, partially in section, taken along section lines 13-13 in FIG. 2, more particularly illustrating a pair of spaced-apart sheath flanges provided in the cleaner sheath element of the laparoscopic lens cleaner and a laparoscope (in phantom) inserted in the cleaner sheath and engaging the sheath flanges.

Prior to the laparoscopic surgical procedure, the laparoscopic lens cleaner 1 is positioned on the lens shaft 61 of the laparoscope 56. This is accomplished typically by extending the lens shaft 61 of the laparoscope 56 through the sheath interior 4 of the cleaner sheath 2, as illustrated in FIG. 5, until the ring gasket 10 of the cleaner sheath 2 sealingly engages the laparoscope housing 57, as illustrated in FIG. 6. The attachment clip 14 on the cleaner sheath 2 is typically caused to engage the laparoscope housing 57, such as by, for example, engaging a housing notch 58 on the laparoscope housing 57 in the locking configuration of the attachment clip 14, as illustrated in FIG. 6, to detachably fasten the cleaner sheath 2 to the laparoscope 56. As illustrated in FIG. 13, when the cleaner sheath 2 is positioned on the lens shaft 61, the distal end of the lens shaft 61 engages the sheath flange or flanges 8 in the sheath interior 4 of the cleaner sheath 2. Furthermore, as illustrated in FIGS. 8 and 9, the laparoscope lens 62 (shown in phantom) is located adjacent to and directly in the discharge flow path of the fluid discharge nozzle 20 of the fluid conduit 18 and of the gas discharge nozzle 28 of the gas conduit 26. As illustrated in FIG. 1, the fluid connecting conduit 32 and the gas connecting conduit 36 of the laparoscopic lens cleaner 1 are connected to the fluid pump and supply apparatus 40 and the gas pump and supply apparatus 46, respectively, typically through the respective conduit connectors 33 and 37.

Figure 7:
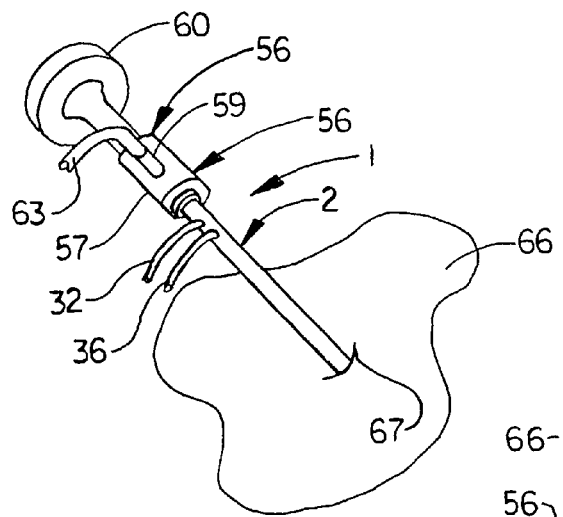
FIG. 7 is a perspective view of a laparoscope extending through an incision in a patient (partially in section), with the laparoscopic lens cleaner fitted on the laparoscope.

The laparoscopic surgical procedure is initiated by prepping the patient 66 typically in conventional fashion. As illustrated in FIG. 7, an incision 67 is cut typically through the abdominal wall of the patient 66. The cleaner sheath 2 of the laparoscopic lens cleaner 1, extending over the lens shaft 61 of the laparoscope 56, is inserted through the incision 67, with the laparoscope housing 57 of the laparoscope 56 remaining outside the patient 66. Inside the abdomen or pelvis of the patient 66, anatomical structures (not illustrated) which are to be viewed, repaired, removed or manipulated in the surgical field during the laparoscopic surgical procedure are typically initially sighted through the camera viewfinder 60 of the laparoscope 56. These images are also transmitted to the television monitor (not illustrated) by the laparoscopic camera (not illustrated), which is connected to the laparoscope housing 57 typically through the camera cord 63 and camera attachment nipple 59, and the images are displayed on the television monitor. Various laparoscopic surgical instruments (not illustrated) are extended into the patient 66 typically through cannula sleeves (not illustrated) which are inserted through the incision 67 and/or through a separate incision or incisions (not illustrated) which are cut through the abdominal wall of the patient 66. Therefore, the laparoscope 56 is used by the surgical team to view the surgical field, including the anatomical structure or structures typically in the abdominal or pelvic region of the patient 66, on the television monitor as the laparoscopic surgical instruments are manipulated to repair, remove or otherwise manipulate the structure or structures.

Throughout the laparoscopic surgical procedure, biological tissue or matter (not illustrated) has a tendency to enter the distal opening 7 of the cleaner sheath 2 of the laparoscopic lens cleaner 1 and contact the laparoscope lens 62 of the laparoscope 56. This tends to obscure the images of the surgical field as they are displayed on the television monitor. Therefore, the biological tissue or matter can be cleaned from the laparoscope lens 62 typically as follows. The fluid pump and supply apparatus 40 (FIG. 1) is initially operated to pump a cleaning fluid 50, such as saline solution, for example, through the fluid connecting conduit 32 and the fluid distribution segment 19 and fluid discharge nozzle 20, respectively, of the fluid conduit 18. As illustrated in FIG. 8, the cleaning fluid 50 is discharged from the fluid discharge nozzle 20 through the nozzle openings 22 (FIG. 11) in a spray pattern, or alternatively, through the single nozzle opening 23 (FIG. 12) in a single stream, against and across the surface of the laparoscope lens 62. The cleaning fluid 50 dislodges the tissue or other matter (not illustrated) from the laparoscopic lens 62, substantially clearing the images of the surgical field which are displayed on the television monitor.

After the cleaning fluid 50 is discharged against the laparoscope lens 62, residual cleaning fluid 50 can be dried from the laparoscopic lens 62 as illustrated in FIG. 9, typically as follows. The gas pump and supply apparatus 46 (FIG. 1) is initially operated to pump a drying gas 52, such as carbon dioxide, for example, through the gas connecting conduit 36 and the gas distribution segment 27 and gas discharge nozzle 28, respectively, of the gas conduit 26. As illustrated in FIG.

9, the drying gas 52 is discharged from the gas discharge nozzle 28, against and across the surface of the laparoscopic lens 62. The drying gas 52 dries the residual cleaning fluid 50 from the laparoscopic lens 62 to prevent the residual cleaning fluid 52 from obscuring the images of the surgical field as they are displayed on the television monitor. The fluid pump and supply apparatus 40 and the gas pump and supply apparatus 46 can be operated as often as is necessary to rinse and dry, respectively, the laparoscope lens 62 of the laparoscope 56 and maintain clarity of the surgical field as it is displayed on the television monitor. It is understood that the apparatus can be disposable, as desired.

While the preferred embodiments have been described above, it will be recognized and understood that various modifications can be made and the appended claims are intended to cover all such modifications which may fall within the spirit and scope of the invention.

Having described my disclosure with the particularity set forth above, I claim:

1. A laparoscopic lens cleaner for a laparoscope having a laparoscope lens, comprising:
   an elongated cleaner sheath having a sheath interior adapted to receive the laparoscope;
   a fluid conduit carried by said cleaner sheath;
   a fluid discharge nozzle provided in said sheath interior and communicating with said fluid conduit and oriented to discharge a cleaning fluid against the laparoscope lens;
   a gas conduit carried by said cleaner sheath; and
   a gas discharge nozzle provided in said sheath interior and communicating with said gas conduit and oriented to discharge a drying gas against the laparoscope lens.

2. The laparoscopic lens cleaner of claim 1 wherein said cleaner sheath comprises a generally tubular sheath wall defining said sheath interior and wherein said fluid conduit and said gas conduit each extends within and along said sheath wall.

3. The laparoscopic lens cleaner of claim 1 further comprising at least one sheath flange carried by said cleaner sheath and extending into said sheath interior.

4. The laparoscopic lens cleaner of claim 1 further comprising an attachment clip carried by said cleaner sheath.

5. The laparoscopic lens cleaner of claim 1 further comprising a ring gasket carried by said cleaner sheath.

6. The laparoscopic lens cleaner of claim 1 further comprising a nozzle plate carried by each of said fluid discharge nozzle and said gas discharge nozzle and at least one nozzle opening provided in said nozzle plate.

7. The laparoscopic lens cleaner of claim 6 wherein said at least one nozzle opening comprises a plurality of nozzle openings provided in said nozzle plate.

8. A laparoscopic lens cleaner for a laparoscope having a laparoscope lens, comprising:
   a generally elongated, tubular cleaner sheath having a sheath wall and a sheath interior defined by said sheath wall and adapted to receive the laparoscope;
   a fluid conduit carried by said cleaner sheath;
   a fluid discharge nozzle communicating with said fluid conduit and extending into said sheath interior and oriented to discharge a cleaning fluid against the laparoscope lens;
   a fluid connecting conduit communicating with said fluid conduit and extending from said cleaner sheath;
   a gas conduit carried by said cleaner sheath;
   a gas discharge nozzle communicating with said gas conduit and extending into said sheath interior and oriented to discharge a drying gas against the laparoscope lens;
   a gas connecting conduit communicating with said gas conduit and extending from said cleaner sheath;
   a fluid pump and supply apparatus disposed in fluid communication with said fluid conduit and adapted to pump the cleaning fluid through said fluid conduit and from said fluid discharge nozzle; and
   a gas pump and supply apparatus disposed in fluid communication with said as conduit and adapted to pump the drying gas through said gas conduit and from said gas discharge nozzle.

9. The laparoscopic lens cleaner of claim 8 wherein said cleaner sheath comprises a generally tubular sheath wall defining said sheath interior and wherein said fluid conduit and said gas conduit each extends within and along said sheath wall.

10. The laparoscopic lens cleaner of claim 8 further comprising at least one sheath flange carried by said cleaner sheath and extending into said sheath interior.

11. The laparoscopic lens cleaner of claim 8 further comprising a spring-biased attachment clip carried by said cleaner sheath.

12. The laparoscopic lens cleaner of claim 8 further comprising a ring gasket carried by said cleaner sheath.

13. The laparoscopic lens cleaner of claim 8 further comprising a nozzle plate carried by each of said fluid discharge nozzle and said gas discharge nozzle and at least one nozzle opening provided in said nozzle plate.

14. The laparoscopic lens cleaner of claim 13 wherein said at least one nozzle opening comprises a plurality of nozzle openings provided in said nozzle plate.

15. A laparoscopic lens cleaner comprising:
   a laparoscope having a laparoscope lens;
   an elongated cleaner sheath having a sheath wall and a sheath interior defined by said sheath wall and receiving said laparoscope;
   a fluid conduit including an elongated fluid distribution segment having an inlet end and an outlet end extending within and along said sheath wall of said cleaner sheath and having a diameter larger than a thickness of said sheath wall;
   a fluid pump and supply apparatus communicating with said inlet end of said fluid distribution segment and adapted to pump a cleaning fluid through said fluid conduit;
   a fluid discharge nozzle communicating with said outlet end of said fluid distribution segment and extending into said sheath interior and oriented toward said laparoscope lens, said fluid discharge nozzle adapted to discharge the cleaning fluid against the laparoscope lens;
   a gas conduit including an elongated gas distribution segment having an inlet end and an outlet end extending within and along said sheath wall of said cleaner sheath and having a diameter larger than a thickness of said sheath wall;
   a gas pump and supply apparatus communicating with said inlet end of said gas distribution segment and adapted to pump a drying gas through said gas conduit; and
   a gas discharge nozzle communicating with said outlet end of said gas distribution segment and extending into said sheath interior and oriented toward said laparoscope lens, said gas discharge nozzle adapted to discharge the drying gas against the laparoscope lens.

16. The laparoscopic lens cleaner of claim 15 wherein said fluid conduit and said gas conduit are disposed in generally diametrically-opposed relationship with respect to each other on opposite sides of said sheath interior of said cleaner sheath.

17. The laparoscopic lens cleaner of claim 15 further comprising an elongated, flexible fluid connecting conduit communicating with said inlet end of said fluid distribution segment and an elongated, flexible gas connecting conduit communicating with said inlet end of said gas distribution segment, and wherein said fluid pump and supply apparatus is connected to said fluid connecting conduit and said gas pump and supply apparatus is connected to said gas connecting conduit.

* * * * *